United States Patent [19]

Hanson et al.

[11] Patent Number: 4,537,194
[45] Date of Patent: Aug. 27, 1985

[54] ICE APPLICATOR FOR MEDICINAL PURPOSES

[76] Inventors: Oliver D. Hanson, 2255 Viking Bldg. NW., Cedar, Minn. 55011; Donald R. Nicolai, Box 415; Les O. Strong, 240 Mississippi, both of Monticello, Minn. 55362

[21] Appl. No.: 588,505

[22] Filed: Mar. 12, 1984

[51] Int. Cl.³ .............................................. A61F 7/00
[52] U.S. Cl. .................................... 128/399; 128/403; 249/84; 249/120; 249/134; 426/66
[58] Field of Search .................... 128/399, 403; 249/83, 249/84, 96, 119, 120, 127, 128, 130, 134; 426/66, 100, 101, 249

[56] References Cited

U.S. PATENT DOCUMENTS

| | | | |
|---|---|---|---|
| 1,021,437 | 3/1912 | Vallone | 249/83 |
| 1,948,147 | 2/1934 | Warren | 249/119 X |
| 1,990,198 | 2/1935 | Murphy | 249/83 |
| 3,176,053 | 3/1965 | DiStasio | 249/134 UX |
| 3,399,858 | 9/1968 | Lucker | 249/134 X |

FOREIGN PATENT DOCUMENTS 1451094 9/1976 United Kingdom ............... 426/66

*Primary Examiner*—Anton O. Oechsle
*Attorney, Agent, or Firm*—Orrin M. Haugen; Thomas J. Nikolai; Douglas L. Tschida

[57] ABSTRACT

This invention relates to the field of medical instruments and particularly to an applicator used to apply a frozen solid such as ice to a wound or injury to treat the wound or injury. The invention is comprised of first and second container means. The first container means has an open top of a predetermined size, a tapered side wall and a bottom having a central opening therethrough. The second container means has a shape conforming at least in part to that of the first container means, an open top and a closed bottom. The two container means are fitted together by placing the bottom of the first means into the top of the second container means. The device can then be filled with liquid and frozen until needed. When in use as an applicator, the second container means is removed and the first container means serves as a handle for applying the frozen solid.

11 Claims, 4 Drawing Figures

ICE APPLICATOR FOR MEDICINAL PURPOSES

BACKGROUND OF THE INVENTION

Often effective for controlling pain, muscle spasms, and swelling and aiding in the process of healing is the application of a cold substance such as ice to an injured area. In the past, ice was commonly applied to arthritic joints, burns, bruises or bumps by wrapping them in a cloth and applying the cloth to the injured areas. This method had several disadvantages. It was awkward and ineffective in that the user's hand was subjected to the low temperature of the frozen liquid. Further, it was difficult to control the amount of pressure being placed upon the wounded area during the massage.

BRIEF DESCRIPTION OF THE INVENTION

The present invention comprises an inexpensive, safe, simple instrument by which ice or some other frozen substance can be applied to burns, arthritic joints or sports-related injuries in a safe, clean, comfortable, efficient and convenient manner and without discomfort to the person applying the treatment. The device is comprised of first and second container means. The first container means is of a generally frustoconical or frustopyramidal configuration having an open top, a side wall or side walls, and a bottom with a lip portion surrounding the central opening. For reasons which will become more apparent from the following description of the preferred embodiment, the first container means is preferably formed from a foam plastic material, possessing good thermal insulation properties. The second container means has a fully closed bottom, a side wall or side walls, and a fully opened top. The two container means are designed so that the open top of the second container means can be slipped over the bottom portion of the first container means until it forms a seal with the first container means at a point along the tapered side wall of the first container means. With this novel apparatus, a frozen solid suitable for treating a wound or injury can be formed around the lip at the bottom of the first container means by (1) placing the second container means over the bottom of the first container means, (2) filling the assembly with liquid, and (3) cooling the liquid until it freezes. To apply the frozen solid to an injured area, the second container means is removed and the top portion of the side wall of the first container means serves as a handle. Because formed from a good thermal insulator, the user's hand is not subjected to the low temperature of the frozen liquid during the treatment process.

Various advantages and features of novelty which characterize the invention are pointed out with particularity in the claims annexed hereto and form a part hereof. However, for a better understanding of the invention, its advantages and objects obtained by its use, reference should be had to the drawings which form a further part hereof, and to the accompanying descriptive matter, in which there are illustrated and describe certain preferred embodiments of the invention.

BRIEF DESCRIPTION OF THE DRAWINGS

In the drawings, in which like reference numerals identify like elements throughout the several views.

DESCRIPTION OF THE PREFERRED EMBODIMENT

Figure 1:
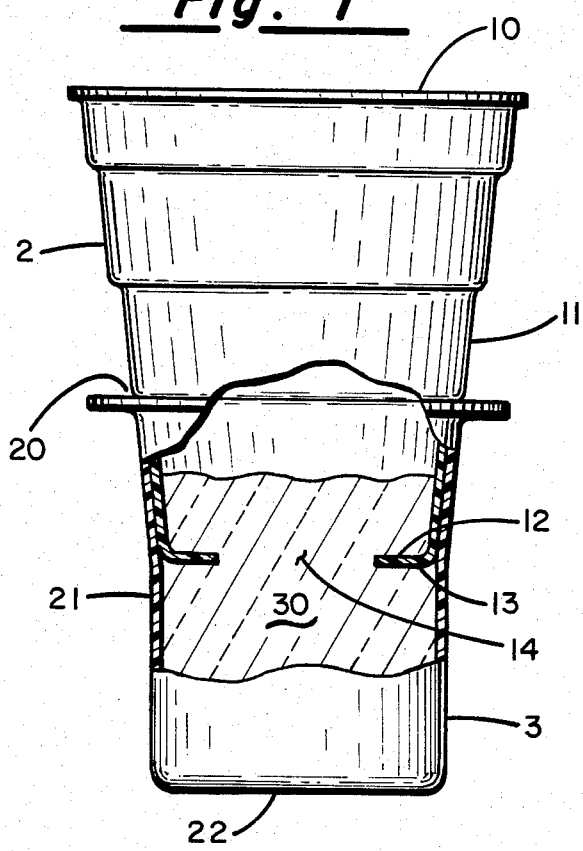
FIG. 1 is a partially cross-sectional side view of one embodiment of the device when assembled.

Referring now to FIG. 1 of the drawings, an ice applicator according to the invention is shown to comprise a first container means 2 and a second container means 3. The container means 2 as shown in the drawings has a generally frustoconical shape. Those skilled in the art will recognize that it could also have a generally frustopyramidal shape. Container means 2 also has an open top 10, a tapered side wall 11 and a bottom 12. The bottom 12 has an annular lip portion 13 defining a center opening 14. In the preferred embodiment the container means 2 is constructed of an insulative material such as foamed polystyrene. Also, bottom 12 has a smaller perimeter than does top 10. Stepped portions are present on the side walls of container means 2 to aid in maintaining a sealing engagement between container means 2 and container means 3 when assembled as shown in FIG. 1.

Figure 2:
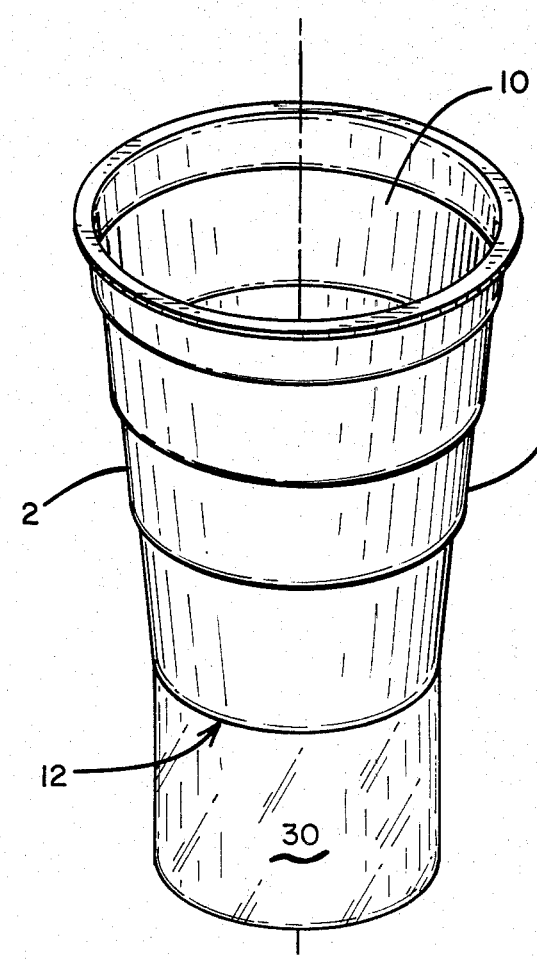
FIG. 2 is a perspective view of the parts of one embodiment when unassembled.
Figure 2:
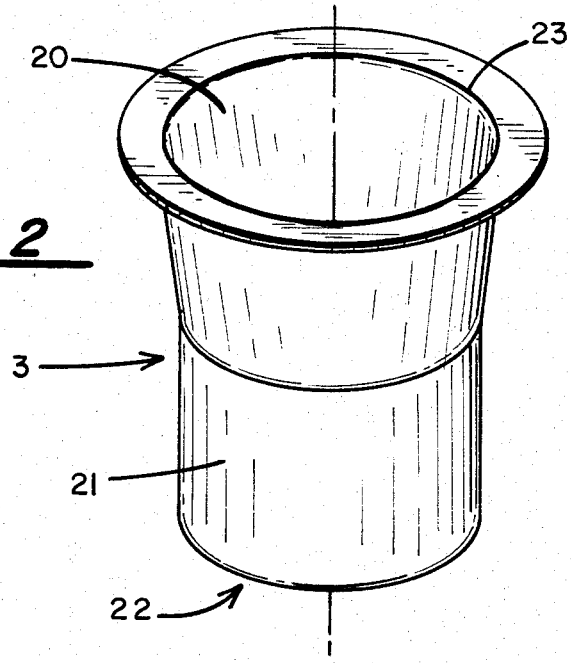

In the preferred embodiment the second container means 3 is either cylindrical or frustoconical in shape and is constructed out of a plastic material having good release properties. One skilled in the art will recognize the container means 3 could have a wide variety of shapes and could be constructed from many different materials and still perform as required. As shown in FIG. 2, container means 3 has an open top 20, a side wall 21 and a fully closed bottom 22. Opening 20 has a larger diameter than that of the bottom 12 of container means 2. Opening 20 has a smaller diameter than the top 10 of container means 2. Opening 20 has the same inside diameter as the outside diameter of tapered side wall 11 at a point approximately $\frac{1}{4}$ to $\frac{1}{2}$ of the distance from the bottom of container means 2 to the top of container means 2.

When the device is used, the bottom of container means 2 is placed within the top of container means 3 until a sealing engagement is achieved between the top rim 23 of side wall 21 of container means 3 and the tapered side wall 11 of container means 2. When assembled as described above, a space designated as 30 in the drawings exists between the bottom 12 of container means 2 and bottom 22 of container means 3. Water is then placed in the device until container means 3 is full and container means 2 is $\frac{1}{4}$ to $\frac{3}{4}$ full. The device is then cooled until the water is frozen. When ice forms, lip 13 becomes embedded in the ice.

When it becomes desirable to apply ice to burns, sports-related injuries, arthritic pain some other trauma, container means 3 is slipped off of the bottom portion of container means 2 and the first container means 2 can then be gripped and used as a handle to apply the ice, which is formed around the lip 13, to the injured area. Being formed from a good thermal insulator, the user's hand does not become chilled.

Often it is important to medicate an injured area as well as chill it to enhance healing and reduce pain and swelling. Although the invention was originally contemplated for use with ice formed from pure, clean water, it could also be used with numerous other mixtures and compounds containing a medication.

Figure 3:
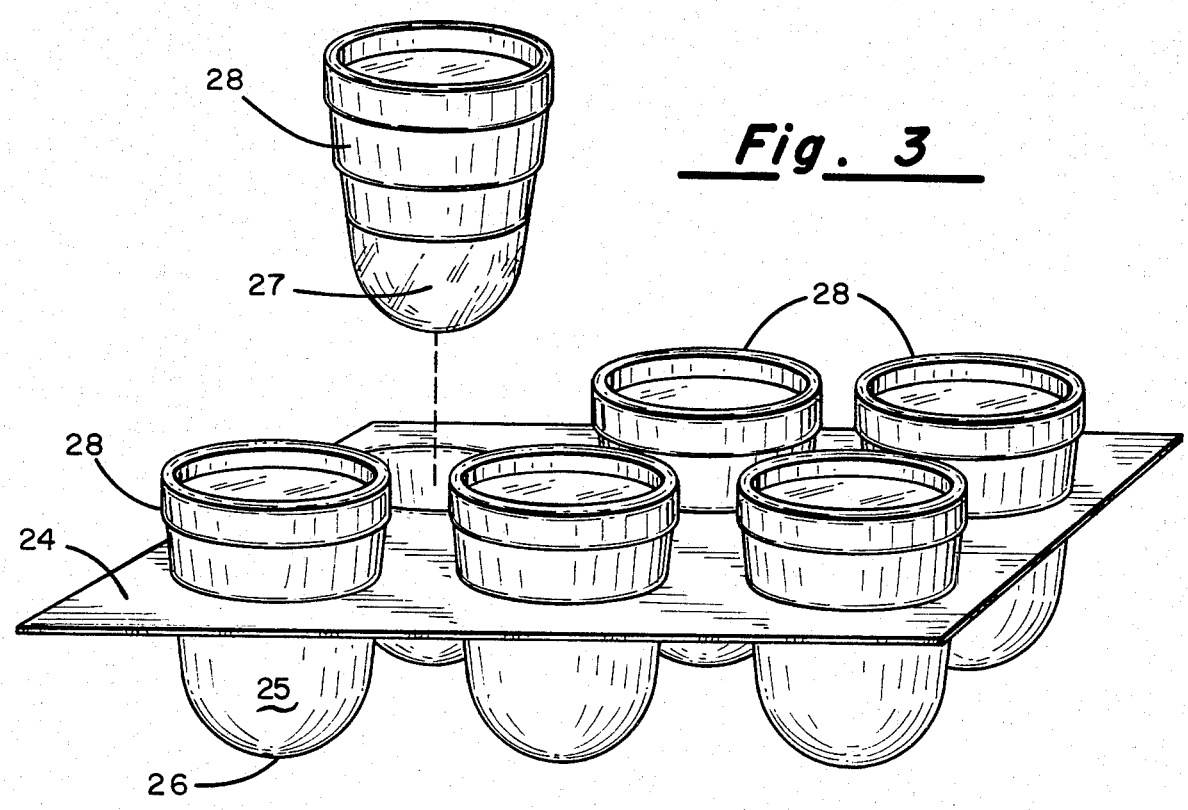
FIG. 3 is a perspective view of a second embodiment in which a plurality of the devices are joined together.
Figure 4:
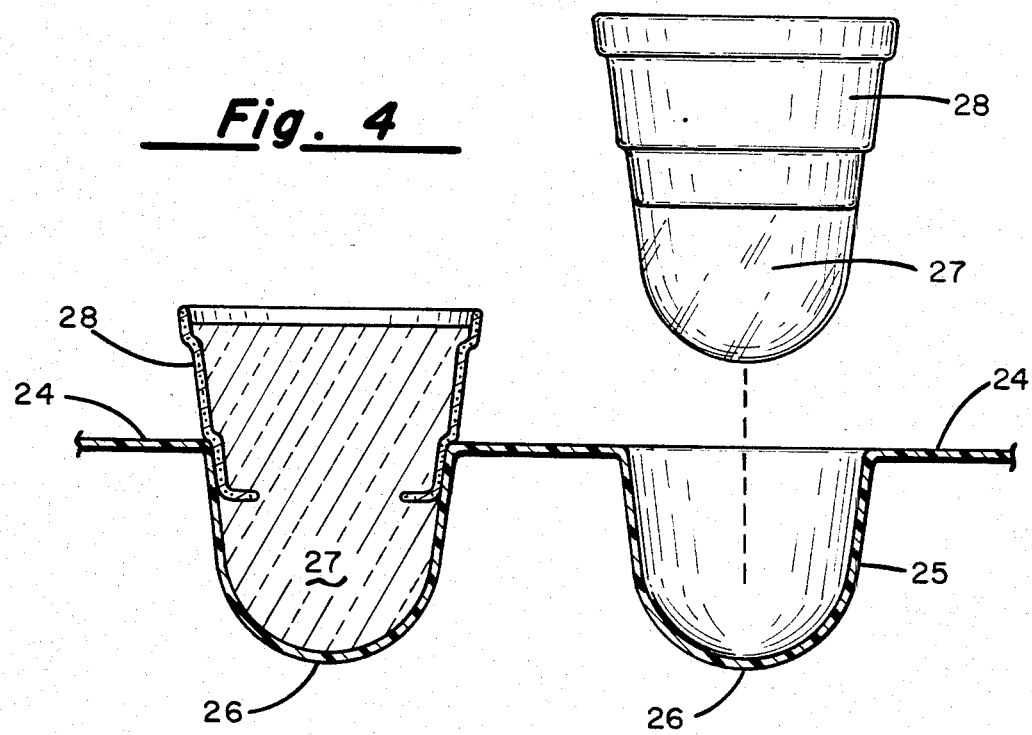
FIG. 4 is a partial cross-sectional view of the second embodiment.

FIGS. 3 and 4 show an alternative embodiment which incorporates a tray 24, preferably made out of plastic, for retaining or joining a plurality of lower container means 25. The tray 24 can be made integral with the lower container means 25 and supported thereby. The principal advantage of this embodiment is that the base 26 of each lower container means 25 can be rounded rather than flat, thus eliminating sharp edges in the portion of the frozen solid 27 to be applied to the painful or injured area. In this alternative embodiment, container means 28 may, again, be used as a handle when applying the frozen solid 27 to the injured area.

Numerous characteristics and advantages of the invention have been set forth in the foregoing description, together with details of structure and function of the invention, and novel features thereof are pointed out in the appended claims. The disclosure, however, is illustrative only, and changes may be made in detail, especially in matters of shape, size and arrangements of parts, within the principle of the invention, to the full extent indicated by the broad, general meaning of the terms in which the appended claims are expressed.

We claim:

1. An applicator assembly for making, storing and applying a frozen solid to an injured area comprising first container means and second container means; said first container means having an open top of a predetermined size, a tapered side wall and a bottom of a size less than said predetermined size and having a central opening therethrough; said second container means having a shape conforming at least in part to the shape of said first container means and including a closed bottom, a side wall and a top with an opening of a size which will allow a top portion of the second container means to be slipped over a bottom portion of the first container means and to engage the side wall of the first container means a predetermined distance above the said bottom of said first container forming a seal.

2. An applicator assembly of claim 1 in which the first and second container means each have a frustoconical shape.

3. An applicator assembly of claim 1 in which the first container means has a frustoconical shape and the second container means has a cylindrical shape.

4. An applicator assembly of claim 1 in which the first and second container means have a frustopyramidal shape.

5. An applicator assembly of claim 1 in which the first container means is constructed of an insulative material.

6. An applicator assembly of claim 5 in which said insulative material is foamed polystyrene.

7. An applicator assembly of claim 1 in which said second container means is constructed of a smooth, water impervious plastic material.

8. An applicator assembly of claim 1 in which the bottom portion of said second container means is of such a shape that the portion of the frozen solid formed in the applicator which is applied to the injured area is free of sharp edges.

9. An applicator assembly used for applying a frozen solid to an injured area comprising first container means of a frustoconical shape constructed out of an insulative material and second container means; said first container means having an open top, a side wall and a bottom in the form of an annular lip surrounding a central opening; said second container means having a closed bottom, a side wall and a top with an opening of a size which will allow the top of the second container means to be slipped over the bottom of the first container means and engage the side wall of the first container means a predetermined distance above said bottom of said container and forming a seal.

10. An applicator assembly of claim 9 in which said insulative material is foamed polystyrene.

11. An applicator assembly of claim 9 in which the bottom portion of the second container means is of such a shape that the portion of the frozen solid formed in the applicator which is applied to the injured area is free of sharp edges.

* * * * *